US012717048B2

(12) United States Patent
Hilderscheid et al.

(10) Patent No.: US 12,717,048 B2
(45) Date of Patent: Aug. 25, 2026

(54) ENERGY SUPPLY CIRCUIT FOR AN X-RAY DEVICE, X-RAY DEVICE AND METHOD FOR OPERATING AN X-RAY DEVICE

(71) Applicant: Siemens Healthineers AG, Forchheim (DE)

(72) Inventors: Thomas Hilderscheid, Altdorf (DE); Shameem Kabir Chaudhury, Nuremberg (DE); Andreas Urban, Eckental (DE); Waseem Haider, Erlangen (DE); Min Qiu, Shanghai (CN); Zhu Gao Ding, Shanghai (CN); Alfons Eismann, Pinzberg (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 19/214,130

(22) Filed: May 21, 2025

(65) Prior Publication Data

US 2025/0362417 A1 Nov. 27, 2025

(30) Foreign Application Priority Data

May 23, 2024 (DE) ..................... 10 2024 204 761.9

(51) Int. Cl.

*G01T 1/175* (2006.01)
*A61B 6/00* (2006.01)
*A61B 6/42* (2024.01)
*A61B 6/58* (2024.01)
*G01T 1/24* (2006.01)

(52) U.S. Cl.

CPC ............ *G01T 1/175* (2013.01); *A61B 6/4241* (2013.01); *A61B 6/56* (2013.01); *A61B 6/58* (2013.01); *G01T 1/24* (2013.01)

(58) Field of Classification Search

CPC .......... G01T 1/175; A61B 6/4241; A61B 6/56

See application file for complete search history.

(56) References Cited

U.S. PATENT DOCUMENTS 5,434,900 A * 7/1995 Tanaka .................. A61B 6/548 378/207
2015/0182183 A1 7/2015 Ergler et al.
2015/0212215 A1* 7/2015 Goderer ................. G01T 1/244 250/370.15

(Continued)

FOREIGN PATENT DOCUMENTS

CN 110494770 A 11/2019
CN 211606905 U 9/2020

(Continued)

OTHER PUBLICATIONS

German Office Action and English translation thereof for German Application No. 10 2024 204 761.9 mailed Feb. 15, 2025.

(Continued)

*Primary Examiner* — Hugh Maupin
(74) *Attorney, Agent, or Firm* — Harness, Dickey & Pierce, P.L.C.

(57) ABSTRACT

One or more example embodiments relates to an energy supply circuit for an X-ray device, having a voltage supply unit and a monitoring unit, wherein the voltage supply unit has an operating path and a maintenance path. One or more example embodiments relates to an X-ray device and a method for operating an X-ray device.

19 Claims, 3 Drawing Sheets

(56) References Cited

U.S. PATENT DOCUMENTS

| | | | |
|---|---|---|---|
| 2017/0322619 | A1 | 11/2017 | Eismann et al. |
| 2018/0292551 | A1 | 10/2018 | Danielsson et al. |
| 2021/0085278 | A1 | 3/2021 | Chaudhury et al. |
| 2023/0181130 | A1 | 6/2023 | Chaudhury et al. |
| 2023/0225694 | A1 | 7/2023 | Chaudhury et al. |

FOREIGN PATENT DOCUMENTS

| | | | |
|---|---|---|---|
| CN | 111864888 | A | 10/2020 |
| CN | 112731999 | A | 4/2021 |
| DE | 102013227214 | A1 | 7/2015 |
| DE | 102016207904 | A1 | 11/2017 |
| DE | 102013227214 | B4 | 6/2021 |
| DE | 102021214335 | B3 | 3/2023 |
| DE | 102022200649 | A1 | 7/2023 |
| EP | 3795081 | A1 | 3/2021 |

OTHER PUBLICATIONS

German Decision to Grant and English translation thereof for German Application No. 10 2024 204 761.9 mailed May 28, 2025.

* cited by examiner

VS.C
CS.N
CS.E
PS.N
PS.E
SU
R
RG
FC
1
CU

PROV-VI
DET-VI
PROV-VB
PROV-VE 49
47
PRVS
43
39
41
35
37
CU
1
BP
EP
SU
SV
SQ
SIG
33
32

ENERGY SUPPLY CIRCUIT FOR AN X-RAY DEVICE, X-RAY DEVICE AND METHOD FOR OPERATING AN X-RAY DEVICE

CROSS-REFERENCE TO RELATED APPLICATION(S)

The present application claims priority under 35 U.S.C. § 119 to Germany Patent Application No. 10 2024 204 761.9, filed May 23, 2024, the entire contents of which is incorporated herein by reference.

FIELD

One or more example embodiments relates to an energy supply circuit for an X-ray device, an X-ray device and a method for operating an X-ray device.

RELATED ART

Computed tomography systems (CT systems, for short) are used for medical imaging investigations on patients. Other expressions for CT systems are also CT device or CT installation. An examination region is thereby irradiated by an X-ray source that is fastened to a rotating part of the CT system from different directions with X-ray radiation and the attenuated X-ray radiation is captured via a co-rotating X-ray detector or count rate detector.

The new generation of photon-counting detectors of CT systems usually comprises one semiconductor material as the sensor material, for example having CdTe, CdZnTe, CdTeSe, CdZnTeSe, CdMnTe, GaAs, Si or Ge. Often, an electric field is generated in the sensor material by applying a bias voltage. The electric field can enable a radiation flow in the sensor material in the presence of X-ray irradiation which can subsequently be evaluated via a directly connected application specific integrated circuit (ASIC). The electric field can lead to a heating of the sensor material. Temperature differences in the X-ray sensor layer, in particular, the sensor material, for example, by way of a switching on or off of the bias voltage, can lead to an undesirable drift and/or image artifacts. To bring the detector, in particular, the sensor material following a switching off and on of the bias voltage, back into a stable, in particular, thermal state, can take up to 24 hours. Meanwhile, measurements cannot be carried out or can only be carried out with a reduced image quality. For this reason, the bias voltage is switched off as seldom as possible, which again leads to an increased energy usage of the CT system.

SUMMARY

One or more example embodiments provides an energy-saving possibility for obtaining a stable, in particular, thermal state of a photon-counting detector.

The object is by way of the subject matter of the independent claims. Advantageous embodiments with suitable developments are the subject matter of the subclaims. Independent of the grammatical term usage, individuals with male, female or other gender identities are included within the term.

BRIEF DESCRIPTION OF THE DRAWINGS

Exemplary embodiments of the invention are illustrated in the drawings and are described in greater detail below. In the different figures, the same reference signs are used for the same features. In the drawings.

DETAILED DESCRIPTION

Figure 1:
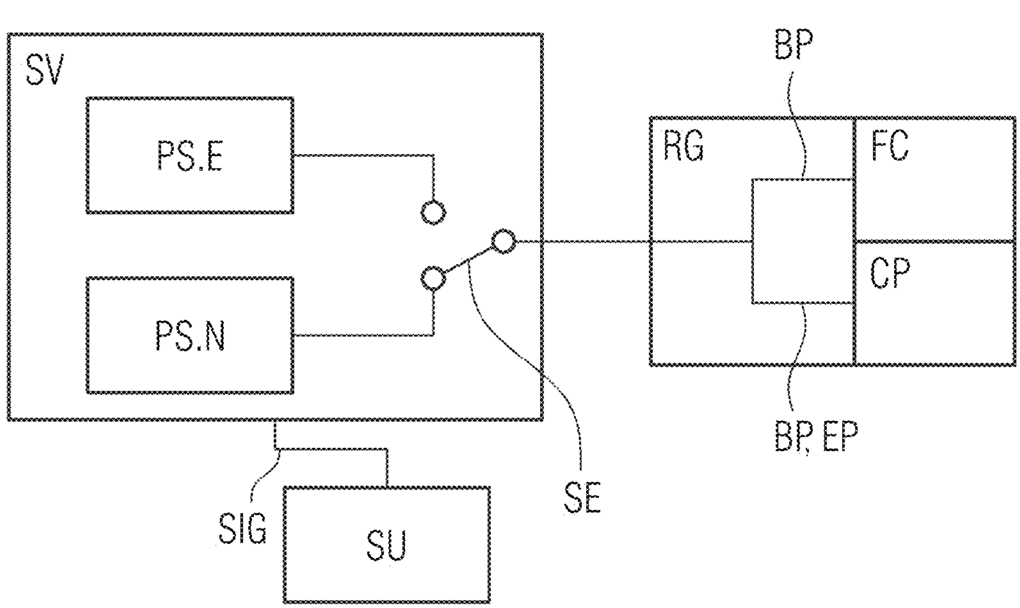
FIGS. 1 to 3 show schematic representations of different advantageous embodiments of a proposed energy supply circuit for an X-ray device.

One or more example embodiments provides an energy supply circuit for an X-ray device. The energy supply circuit has a voltage supply unit and a monitoring unit. Therein, the voltage supply unit has an operating path and a maintenance path. The operating path is configured to supply a plurality of components of the X-ray device for a normal operation. In addition, the maintenance path is configured to supply a partial quantity of the plurality of components of the X-ray device for a maintenance operation. The monitoring unit is configured, via a sensor, to detect an input voltage at a voltage supply input of the voltage supply unit. Furthermore, the voltage supply unit is configured to provide, dependent upon the detected input voltage, an electrical operating voltage via the operating path or an electrical maintenance voltage via the maintenance path to the respective components.

The plurality of components of the X-ray device can comprise, for example, an X-ray source and/or an X-ray detector.

The voltage supply unit can be configured to be fed by at least one voltage source. For this purpose, the voltage supply unit can have a voltage supply input for receiving electrical energy. Advantageously, in an operating state of the energy supply circuit, the at least one voltage source can provide the input voltage to the voltage supply unit, in particular, to the voltage supply input.

The monitoring unit can have a sensor, for example, a voltage sensor which is configured for detecting the electrical input voltage, in particular, a value of the input voltage, at the voltage supply input of the voltage supply unit. Therein, the monitoring unit can be configured, for example, to provide a control signal dependent upon the input voltage detected by way of the sensor, in particular, having a qualitative or quantitative information item relating to the value of the detected input voltage. In particular, the monitoring unit can be configured to provide the control signal dependent upon the detected input voltage to the voltage supply unit.

The operating path can denote an energy transfer path, in particular, for the transfer and supply of electrical energy for a normal operation of the X-ray device. The normal operation can comprise an intended operation, in particular, a recording operation, of the X-ray device, for example, for imaging an examination object. Advantageously, the operating path can be configured to provide an electrical operating voltage provided by the voltage supply unit to all the components of the X-ray device required for the normal operation.

The maintenance path can denote a further energy transfer path, in particular for the transfer of electrical energy for a maintenance operation of the X-ray device. The maintenance operation can advantageously comprise an operation for maintaining and/or stabilizing and/or conditioning at least one subset of the components of the X-ray device.

Advantageously, the maintenance path can be configured to provide an electrical maintenance voltage provided by the voltage supply unit to the subset of the plurality of components of the X-ray device for the maintenance operation.

The maintenance path can be a subpath of the operating path or can be different from the operating path except for the supplying of the subset of the plurality of components of the X-ray device.

The maintenance path can have a lower voltage than the operating path, in particular, a lower voltage requirement and/or a lower energy requirement. In particular, the operating voltage and/or an energy requirement of the operating path can correspond to at least the maintenance voltage and/or an energy requirement of the maintenance path.

The voltage supply unit can be configured, dependent upon the detected input voltage, in particular, dependent upon the control signal, to provide, in a first operating state, the operating voltage via the operating path to the plurality of components of the X-ray device or, in a second operating state, the maintenance voltage via the maintenance path to the subset of the plurality of components of the X-ray device.

The proposed energy supply circuit can advantageously enable an energy-saving maintenance of a stable, in particular, thermal state of the subset of the plurality of components of the X-ray device. In particular, the proposed energy supply circuit can ensure a supply of the subset of the plurality of components of the X-ray device for the maintenance operation, in particular, also during short energy interruptions, for example, during a switch-over between a supply from the power grid and an emergency supply. The energy supply circuit can make do in a hardware-efficient manner, in particular, with minimum additional hardware complexity and/or without additional digital functions. In particular, the proposed energy supply circuit is configured for the detection of an energy-saving operation, wherein components of the X-ray device, for example, components of a gantry would be switched off and the subset of the components, for example, a detector unit, would lose an operating point. By this means, a particularly robust maintenance of the stable state of the subset of the plurality of components of the X-ray device can advantageously be enabled.

In a further advantageous embodiment of the proposed energy supply circuit, the operating path can be configured to supply at least one digital component and at least one analogue component of the X-ray device for a normal operation. In addition, the maintenance path can be configured to supply at least one of the at least one analogue components of the X-ray device for a maintenance operation.

The X-ray device can have at least one digital component, in particular a plurality of digital components and at least one analogue component, in particular, a plurality of digital components. The at least one digital component can comprise, for example, an application specific integrated circuit (ASIC) and/or a programmable integrated circuit (field programmable gate array (FPGA)). The at least one analogue component can comprise, for example, a conditioning unit which is configured for providing an energy for maintaining a maintenance state of a detector unit of the X-ray device.

Advantageously, the operating path can be configured to provide an electrical operating voltage provided by the voltage supply unit to the at least one digital component, in particular, the plurality of digital components and the at least one analogue component, in particular, the plurality of analogue components of the X-ray device, for the normal operation. Furthermore, the maintenance path can be configured to provide an electrical maintenance voltage provided by the voltage supply unit to the at least one, in particular, the plurality of, or each of the at least one analogue components, in particular, the plurality of analogue components of the X-ray device for the maintenance operation. In particular, the maintenance path can be configured to supply the at least one of the at least one analogue components of the X-ray device for the maintenance operation and not to supply the remaining, in particular digital, components during the maintenance operation.

The proposed energy supply circuit can advantageously enable an energy-saving maintenance of a stable, in particular, thermal state of the at least one analogue component of the X-ray device. In particular, the provision of the maintenance voltage for the maintenance operation can take place independently of a starting up of the at least one digital component and/or a configuration process of the at least one digital component.

In a further advantageous embodiment of the proposed energy supply circuit, the operating path and the maintenance path can be different except for the supplying of the subset of the plurality of components of the X-ray device.

Advantageously, the operating path and the maintenance path can be different except for a respective contacting for supplying of the subset of the plurality of components, for example, the at least one of the at least one analogue component of the X-ray device, said contacting being, in particular, different or matching. In particular, the operating path and the maintenance path can comprise a circuit that is different, in particular, disjunct except for the respective contacting for supplying the subset of the plurality of components of the X-ray device. The maintenance path and the operating path can further be configured to have the respective voltage, in particular, the maintenance voltage or the operating voltage applied, in particular, fed by the same voltage supply unit.

The voltage supply unit can be configured, dependent upon the detected input voltage, in particular, dependent upon the control signal, to provide, in a first operating state, the operating voltage via the operating path to the plurality of components of the X-ray device. Furthermore, the voltage supply unit can be configured, dependent upon the detected input voltage, in particular, dependent upon the control signal, to provide, in a second operating state, the maintenance voltage via the maintenance path to the subset of the plurality of components of the X-ray device.

The proposed embodiment can advantageously enable a supplying of the respective components adapted to the respective operation, in particular, the normal operation or the maintenance operation. In particular, via the proposed embodiment, an adaptation of the operating path can be dispensed with.

In a further advantageous embodiment of the proposed energy supply circuit, the maintenance path can be a subpath of the operating path.

Advantageously, the maintenance path can be a subpath, in particular, a part of a circuit of the operating path. The operating path can additionally have a circuit part that is able to be activated selectively, in particular, able to be switched in, which is configured for providing the operating voltage to the remainder of the plurality of components of the X-ray device, in particular, the digital components of the X-ray device. For example, the operating path can have a circuit element that is configured, dependent upon the detected input voltage, in particular, dependent upon the control signal and/or the voltage provided by the voltage supply unit, in particular, the operating voltage or the maintenance voltage, to activate or deactivate the part of the operating path going beyond the maintenance path.

The voltage supply unit can be configured, dependent upon the detected input voltage, in particular, dependent upon the control signal, to provide, in a first operating state, the operating voltage via the operating path to the plurality of components of the X-ray device. Furthermore, the voltage supply unit can be configured, dependent upon the detected input voltage, in particular, dependent upon the control signal, to provide, in a second operating state, the maintenance voltage via the maintenance path to the subset of the plurality of components of the X-ray device.

In particular, the respective voltage can be provided via the maintenance path in the first and the second operating state to the subset of the plurality of components of the X-ray device.

By this means, a circuit complexity can advantageously be minimized.

In a further advantageous embodiment of the proposed energy supply circuit, the monitoring unit can be configured to compare the input voltage with a specified voltage threshold value. Furthermore, if the voltage threshold value is reached or exceeded, the voltage supply unit can provide the electrical operating voltage via the operating path or, if the voltage threshold value is undershot, the voltage supply unit can provide the electrical maintenance voltage via the maintenance path.

The monitoring unit can have a comparator, for example, a voltage comparator which is configured to compare the input voltage, in particular, a value of the input voltage that is applied to the voltage supply unit, in particular momentarily, with the specified voltage threshold value. The value of the input voltage can characterize, for example, a peak, an amplitude, a mean value, in particular, a root mean square (RMS) value or a rectified value of the input voltage. The input voltage can be configured as a DC or an AC voltage. The comparator can comprise, for example, an operational amplifier, an analogue-to-digital converter, a (shunt) reference, an LED and/or an optocoupler.

Advantageously, the monitoring unit can be configured, dependent upon the comparison, to provide the control signal to the voltage supply unit. In particular, if the voltage threshold value is undershot, the monitoring unit can provide the control signal to the voltage supply unit such that the voltage supply unit is triggered to provide the maintenance voltage via the maintenance path. Furthermore, if the voltage threshold value is reached or exceeded, the monitoring unit can provide the control signal to the voltage supply unit such that the voltage supply unit is triggered to provide the operating voltage via the operating path.

The proposed embodiment can advantageously ensure an, in particular automatic, energy-saving maintenance of a stable, in particular thermal, state of the subset of the plurality of components of the X-ray device. In particular, the input voltage can be used as a control signal for the provision of the respective voltage via the respective path, in particular, the operating voltage via the operating path or the maintenance voltage via the maintenance path.

In a further advantageous embodiment of the proposed energy supply circuit, the X-ray device can have a detector unit and a conditioning unit. Therein, the conditioning unit can be configured to provide an energy to maintain a maintenance state of the detector unit. In addition, at least the maintenance path can be configured to supply at least the conditioning unit.

The detector unit can be configured for, in particular, photon-counting detection of X-ray radiation incident upon an X-ray sensitive surface of the detector unit. The detector unit can have the X-ray sensitive surface, in particular, an X-ray detector layer, on its upper side. At least in an operating state, this can be arranged facing toward an X-ray source. Furthermore the X-ray detector layer can be configured for detecting X-rays emitted by the X-ray source.

Advantageously, for this purpose, the conditioning unit can be configured to provide an energy to maintain a maintenance state of the detector unit. The maintenance state can describe a state of the detector unit in which the detector unit is tempered within a predefined temperature range or to a predefined temperature, in particular, above a predefined minimum temperature. Advantageously, the conditioning unit can be configured to provide the energy for tempering the detector unit to the predefined temperature, in particular, above the predefined minimum temperature or to a temperature within the predefined temperature range. The conditioning unit can be configured, for example, for providing electromagnetic and/or thermal energy for maintaining the maintenance state of the detector unit. For this purpose, the conditioning unit can be arranged on the detector unit, in particular, at least partially integrated into the detector unit. Alternatively, the conditioning unit can be arranged spaced from the detector unit, advantageously outside a radiation incidence direction of the X-ray radiation relative to the X-ray sensitive surface of the detector unit.

Advantageously, at least the maintenance path, in particular, the maintenance path and the operating path, can be configured to supply at least the conditioning unit. In particular, the voltage supply unit can be configured to provide the maintenance voltage in the second operating state via the maintenance path at least to the conditioning unit. The conditioning unit can be capable of being activated via the maintenance path, in particular, selectively for the maintenance operation, and for the normal operation, capable of being deactivated.

The proposed embodiment can ensure an improved energy-saving maintenance of a stable, in particular thermal, state of the detector unit.

In a further advantageous embodiment of the proposed energy supply circuit, the detector unit can have a semiconductor material and can be configured for photon-counting detection of X-ray radiation. The conditioning unit can be configured to keep the semiconductor material conditioned in the maintenance state via the energy provided.

The X-ray detector layer can comprise a direct-converting (semiconductor) X-ray sensor layer, for example having CdTe, CdZnTe, CdTeSe, CdZnTeSe, CdMnTe, GaAs, Si or Ge as the semiconductor material. The X-ray detector layer can also comprise a layer with analogue-to-digital converters onto which the X-ray sensor layer is applied, wherein the A/D converter layer can be realized in one or more ASICs. Incident X-ray radiation or photons can be converted into electrical pulses by way of a suitable converter material in the X-ray sensor layer. Incident X-ray radiation is converted in the converter material of the X-ray sensor layer dependent upon the locally deposited energy of an X-ray photon into charge carriers, wherein based upon the charge carriers in a pixel-structured pixel electronics system, a signal, typically an electrical pulse can be generated which is typically further processed in a pixel-wise manner. The electrical pulses can be evaluated by an evaluating electronics system, for example, an ASIC. For example, the incident X-ray radiation can be measured by counting the electrical pulses that are triggered by the absorption of X-ray photons in the converter material. The size or the length of a generated electrical pulse is also typically proportional to the energy of the absorbed X-ray photon. In this way, an item of spectral information can be extracted by way of the comparison of the height or length of the electrical pulse with an energy threshold. Often, photon-counting detector units have a plurality of settable energy thresholds for a comparison of the electrical pulses generated so that energy-resolved measurements are enabled, dependent upon a plurality of energy ranges defined by the energy thresholds. A pixel element can be understood to be a pixel-structured pixel electronics system, i.e. an electronic pixel of the evaluating unit which is coupled via a pixel electrode for a signal-conveying purpose to the X-ray sensor layer and which further processes signals received by the X-ray sensor layer via the respective pixel electrode. A corresponding detection volume in the X-ray sensor layer can be associated with the pixel element, said detection volume being formed by an electric field between a respective sensor pixel electrode and a top electrode which is applied on an opposite side of the X-ray sensor layer, and forms the sensitive detection volume of a pixel element. The electric field can be provided by applying a bias voltage to the respective sensor pixel electrode and the top electrode. The electric field can lead to a heating of the semiconductor material of the X-ray sensor layer. Temperature differences in the X-ray sensor layer, for example, due to a switching on or off of the bias voltage, can lead to an undesirable drift and/or image artifacts.

The proposed embodiment can ensure an improved energy-saving maintenance of a stable, in particular thermal, state of the semiconductor material.

In a further advantageous embodiment of the proposed energy supply circuit, the conditioning unit can be configured to provide the energy for maintaining the maintenance state by heat transfer and/or illumination of the detector unit.

The conditioning unit can have a heating element, for example, a heating wire which is configured for providing heat energy to the detector element for maintaining the maintenance state by way of heat transfer. The provision of the heat energy can take place by way of direct heat transfer between the heating element and the detector unit or via a heat conducting medium, for example, a fluid and/or a heat conducting material. Alternatively or additionally, the conditioning unit can have a light source, in particular, an infrared light source for emitting light, in particular, infrared light for illuminating the detector unit, in particular, the X-ray sensor layer and/or the semiconductor material. Therein, the detector unit, in particular the X-ray sensor layer can be capable of being heated by converting the incident infrared light.

Advantageously, the conditioning unit can be configured to temper the detector unit, in particular, the X-ray sensor layer, by way of the heat transfer and/or the illumination to the predefined temperature or to a temperature within the predefined temperature range. By this means, advantageously, a maintenance of the conditioning of the detector unit can be ensured.

One or more example embodiments provides an X-ray device having an X-ray source, a detector unit, at least one voltage source and a proposed energy supply circuit. Therein, the at least one voltage source optionally provides, in a first operating state, a maintenance voltage or in a second operating state, an operating voltage as an input voltage to the energy supply circuit. In the first operating state, based upon the input voltage, the voltage supply unit provides an electric operating voltage via the operating path to the X-ray source and the detector unit for normal operation, so that via the X-ray source, X-ray radiation can be emitted for irradiating the detector unit and the X-ray radiation can be detected via the detector unit. In the second operating state, based upon the input voltage, the voltage supply unit provides an electric maintenance voltage to a subset of the plurality of components of the X-ray device via the maintenance path for a maintenance operation.

The advantages of the proposed X-ray device substantially correspond to the advantages of the proposed energy supply circuit. Features, advantages or alternative embodiments mentioned herein can also be transferred similarly to the other claimed subject matter and vice versa.

In a further advantageous embodiment of the proposed X-ray device, the X-ray device can have a first and a second voltage source. Therein, the first voltage source can be configured to provide the electrical operating voltage in the first operating state as the input voltage to the energy supply circuit. Furthermore, the second voltage source can be configured to provide the electrical maintenance voltage in the second operating state as the input voltage to the energy supply circuit.

The proposed embodiment can advantageously enable a smaller embodiment of the second voltage source as compared with the first voltage source. In particular, the first voltage source can be adapted to the requirements of the provision of the operating voltage and the second voltage source can be adapted to the requirements of the provision of the maintenance voltage.

In a further advantageous embodiment of the proposed X-ray device, the energy supply circuit can have a detector unit and a conditioning unit. Therein, in the second operating state, based upon the input voltage, the voltage supply unit can provide the electrical maintenance voltage to the conditioning unit via the maintenance path.

In a further advantageous embodiment of the proposed X-ray device, the X-ray device can be configured as a computed tomography system. Therein, the X-ray source and the detector unit can be mounted able to rotate in a defined arrangement.

One or more example embodiments provides a method for operating an X-ray device having an energy supply circuit as proposed. In a first step, an input voltage is provided to the energy supply circuit via at least one voltage source. In a further step, the input voltage at the voltage supply input of the voltage supply unit is detected via the sensor. In a further step, dependent upon the detected input voltage, an electrical operating voltage is provided via the operating path or an electrical maintenance voltage is provided via the maintenance path to the respective components of the X-ray device.

The advantages of the proposed method substantially correspond to the advantages of the proposed energy supply circuit and/or of the proposed X-ray device. Features, advantages or alternative embodiments mentioned herein can also be transferred similarly to the other claimed subject matter and vice versa.

In a further advantageous embodiment of the proposed method, the X-ray device can have an energy supply circuit having a detector unit and a conditioning unit. Therein, the voltage supply unit can provide the operating voltage or the maintenance voltage to the conditioning unit dependent upon the detected input voltage. Therein, in each case, via the conditioning unit, an energy for maintaining the maintenance state of the detector unit can be provided.

FIG. 1 shows a schematic representation of an advantageous embodiment of a proposed energy supply circuit for an X-ray device RG. The energy supply circuit can have a voltage supply unit VS and a monitoring unit SU. Furthermore, the voltage supply unit SU can have an operating path BP and a maintenance path EP. Therein, the operating path BP can be configured to supply a plurality of components FC and CP of the X-ray device 1 for a normal operation. In addition, the maintenance path EP can be configured to store a subset CP of the plurality of components CP and FC of the X-ray device RG for a maintenance operation. The monitoring unit SU can be configured to detect an input voltage at a voltage supply input of the voltage supply unit SV via a sensor. In addition, the monitoring unit SU can be configured to provide a control signal SIG dependent upon the detected input voltage to the voltage supply unit SV. The voltage supply unit SV can be configured to provide, dependent upon the detected input voltage, in particular, dependent upon the control signal SIG, an electrical operating voltage via the operating path BP or an electrical maintenance voltage via the maintenance path EP to the respective components FC and/or CP.

The operating path BP can be configured to supply at least one digital component and at least one analogue component of the X-ray device for a normal operation. In addition, the maintenance path EP can be configured to supply at least one of the at least one analogue components of the X-ray device for a maintenance operation.

The operating path BP and the maintenance path EP can be different except for the supplying of the subset CP of the plurality of components CP and FC of the X-ray device RG. Alternatively, the maintenance path EP can be a subpath of the operating path BP.

The monitoring unit SU can be configured to compare the input voltage with a specified voltage threshold value. Furthermore, if the voltage threshold value is reached or exceeded, the voltage supply unit SV can provide the electrical operating voltage via the operating path BP or, if the voltage threshold value is undershot, the voltage supply unit can provide the electrical maintenance voltage via the maintenance path EP. For example, the monitoring unit SU can be configured to provide the control signal SIG to the voltage supply unit SV dependent upon the comparison.

The voltage supply unit SV can have a first voltage source PS.N and a second voltage source PS.E. Therein, the first voltage source PS.N can be configured for supplying the operating path for the normal operation. Furthermore, the second voltage source PS.E can be configured for supplying the maintenance path for the maintenance operation. The voltage supply unit SV can have, for example, a switch element SE which is configured for switching over between the first and second voltage source PS.N and PS.E for supplying the respective path for the respective operation.

Figure 2:
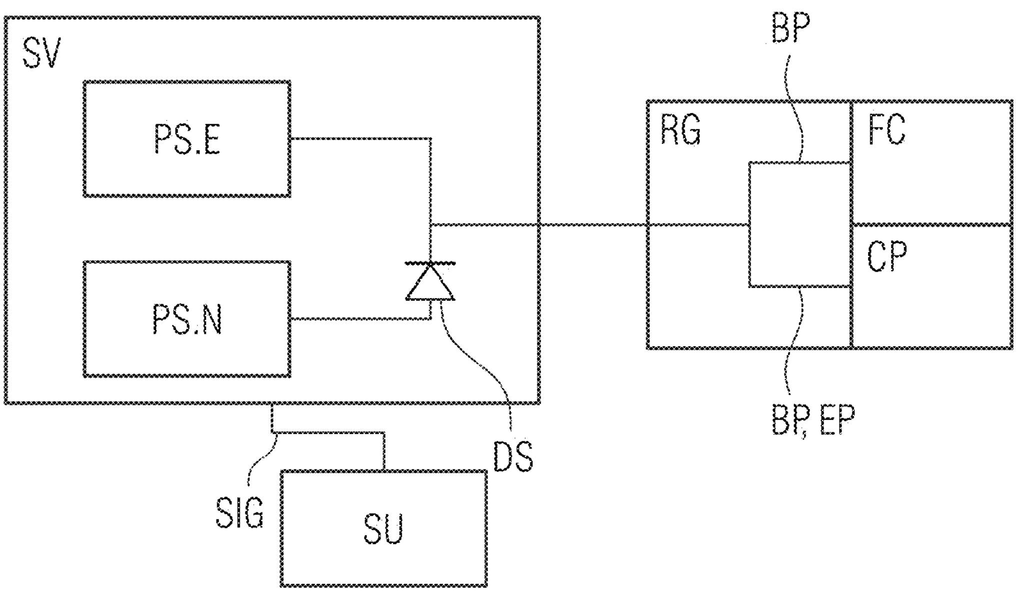

FIG. 2 shows a schematic representation of a further advantageous embodiment of a proposed energy supply circuit for an X-ray device RG.

The voltage supply unit SV can have, for example, a diode DS as the switch element, wherein the diode DS can enable a switch-over between the first and the second voltage source PS.N and PS.E for supplying the respective path for the respective operation.

Figure 3:
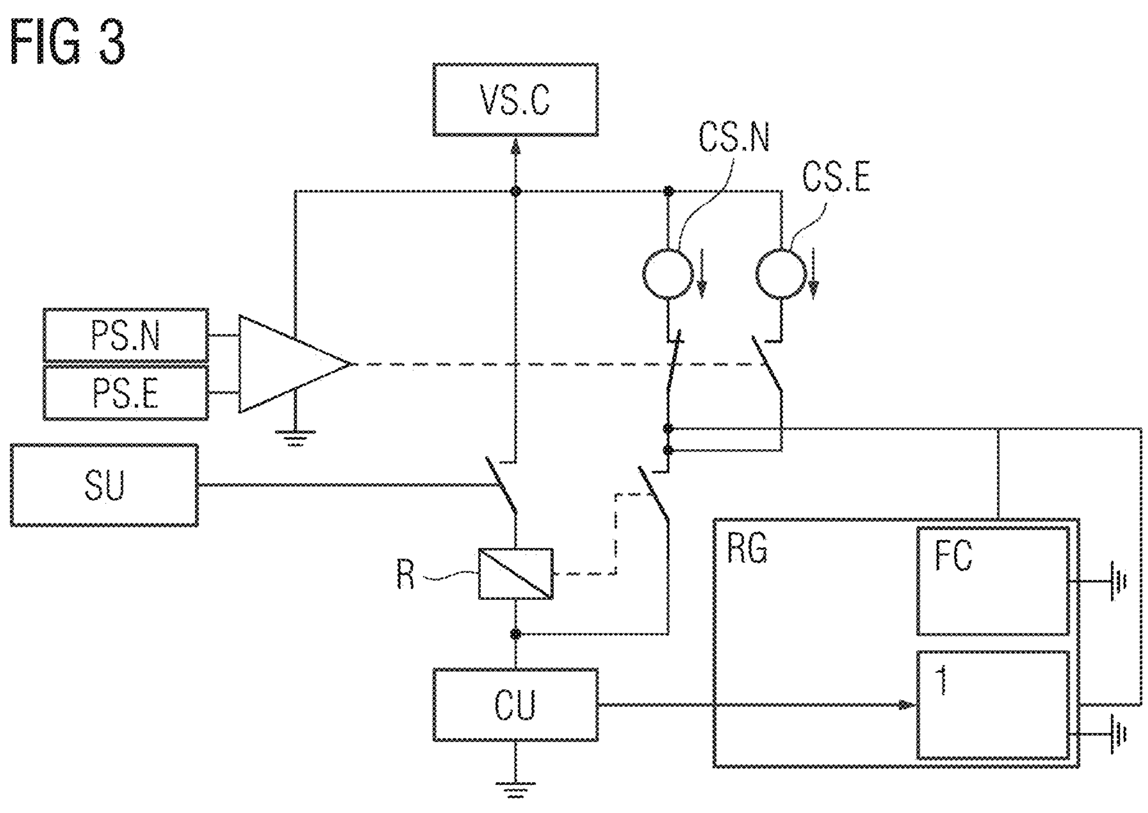

FIG. 3 shows a schematic representation of a further advantageous embodiment of a proposed energy supply circuit for an X-ray device. The X-ray device can therein have a detector unit 1 and a conditioning unit CU. The conditioning unit CU can be configured to provide an energy for maintaining a maintenance state of the detector unit 1. Furthermore, the at least one the maintenance path EP can be configured to supply at least the conditioning unit CU.

The detector unit can have a semiconductor material and can be configured for photon-counting detection of X-ray radiation. Furthermore, the conditioning unit can be configured to keep the semiconductor material conditioned in the maintenance state via the energy provided. The conditioning unit CU can further be configured to provide the energy for maintaining the maintenance state by heat transfer and/or illumination of the detector unit 1.

As shown in FIG. 3, a first current source CS.N can be configured for supplying the operating path for normal operation. Furthermore, a second current source CS.E can be configured for supplying the maintenance path for the maintenance operation. The voltage supply unit VS can further have a first voltage source PS.N for providing an operating voltage for the normal operation und a second voltage source PS.E for providing a maintenance voltage for the maintenance operation. Furthermore, the voltage supply unit can have a third voltage source PS.C for providing a further voltage to the conditioning unit CU. For switching over between the maintenance operation and the normal operation, in particular, the maintenance path and the operating path, a relay R can be used. The conditioning unit CU can ensure, for example, that an earth current, in particular, the maintenance current remains active in the semiconductor material of the detector unit under high voltage, in particular the bias voltage, even during the maintenance operation.

Figure 4:
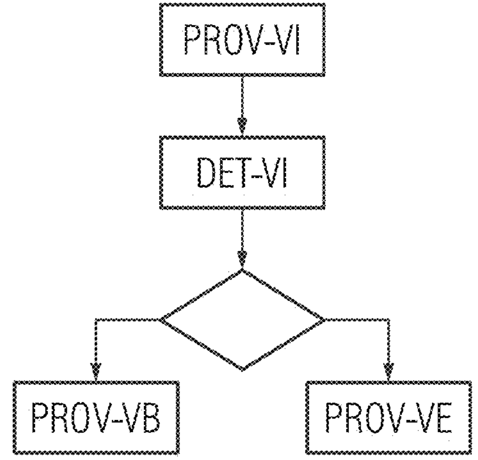
FIG. 4 shows a schematic representation of an advantageous embodiment of a proposed method for operating an X-ray device having an energy supply circuit.

FIG. 4 shows a schematic representation of an advantageous embodiment of a proposed method for operating an X-ray device having a proposed energy supply circuit. In a first step, an input voltage can be provided PROV-VI to the energy supply circuit via at least one voltage source. In a further step, the input voltage at the voltage supply input of the voltage supply unit is detected DET-VI via the sensor. In a further step, dependent upon the detected input voltage, an electrical operating voltage can be provided PROV-VB via the operating path to the plurality of components of the X-ray device or an electrical maintenance voltage can be provided PROV-VE via the maintenance path to the at least one component of the X-ray device.

Advantageously, dependent upon the detected input voltage, in particular, dependent upon the control signal SIG, the voltage supply unit can provide PROV-VB or PROV-VE the operating voltage or the maintenance voltage to the conditioning unit CU. Therein, in each case, via the conditioning unit CU, an energy for maintaining the maintenance state of the detector unit 1 can be provided.

Figure 5:
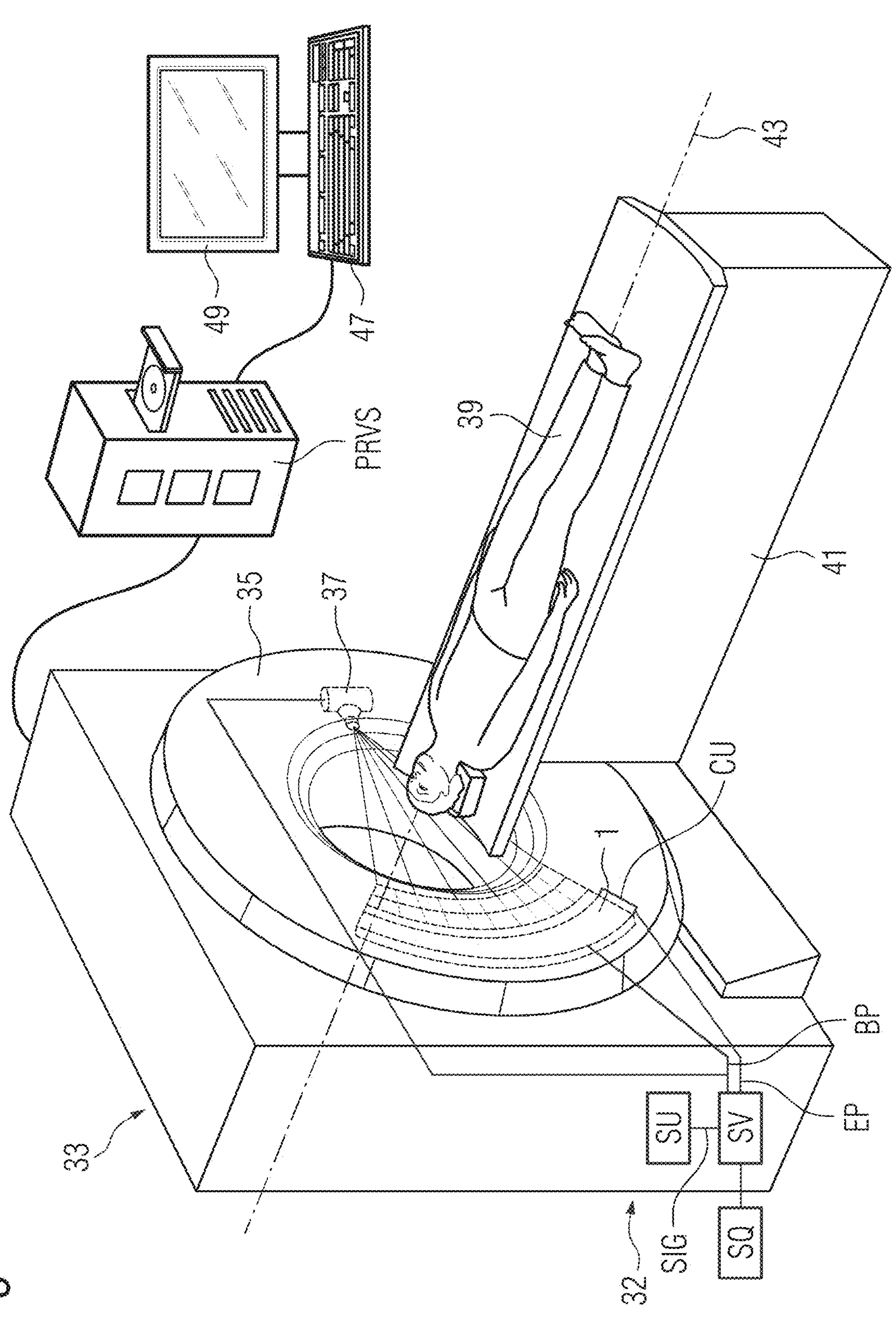
FIG. 5 shows a schematic representation of a CT device as an exemplary embodiment of a proposed X-ray device.

FIG. 5 shows a schematic representation of a CT system 33 as an exemplary embodiment of a proposed X-ray device RG. The CT system 33 can comprise an X-ray source 37, a detector unit 1, at least one voltage source SQ, a proposed energy supply circuit and a processing unit PRVS. Therein, the X-ray source 37 and the detector unit 1, in particular, comprising an X-ray detector, can be arranged opposite one another. The X-ray source 37 can be configured to irradiate the detector unit 1, in particular, the X-ray detector along an X-ray beam incidence direction with X-ray radiation.

The at least one voltage source SQ can optionally provide, in a first operating state, an electrical operating voltage or, in a second operating state, an operating voltage as an input voltage to the energy supply circuit. In particular, the CT system 33 can have a first and a second voltage source (not shown here). Therein, the first voltage source can be configured to provide the electrical operating voltage in the first operating state as the input voltage to the energy supply circuit. Furthermore, the second voltage source can be configured to provide the electrical maintenance voltage in the second operating state as the input voltage to the energy supply circuit.

In the first operating state, based upon the detected input voltage, the voltage supply unit SV can provide the operating voltage via the operating path BP to the X-ray source 37 and the detector unit 1 for normal operation, so that via the X-ray source 37, X-ray radiation can be emitted for irradiating the detector unit 1 and the X-ray radiation can be detected via the detector unit 1. In the second operating state, based upon the detected input voltage, the voltage supply unit SV can provide the maintenance voltage to a subset of the plurality of components of the CT system 33 via the maintenance path EP for a maintenance operation.

Advantageously, the CT system 33 can also have a conditioning unit CU. The conditioning unit CU can be configured to provide an energy for maintaining a maintenance state of the detector unit 1. Furthermore, the maintenance path EP can be configured to supply at least the conditioning unit CU. Furthermore, in the second operating state, based upon the detected input voltage, the voltage supply unit SV can provide the maintenance voltage via the maintenance path EP to the conditioning unit CU.

The CT system 33 can also comprise a gantry 32 with a rotor 35. The X-ray source 37 and the detector unit 1 can be arranged in a defined arrangement on the rotor 35, in particular, integrated into the rotor 35 or fastened on the rotor 35. The rotor 35 can be mounted able to rotate about a rotation axis 43. An examination object 39 to be mapped can be mounted on the patient positioning apparatus 41 and can be moved through the gantry 32 along the rotation axis 43. The processing unit PRVS can be used for controlling the CT system 33 and for calculating sectional images or volume images of the examination object 39. An input facility 47, for example, a keyboard and an output apparatus 49, for example, a screen and/or a display can be connected to the processing unit PRVS, in particular, for signal-conveying purposes. The input facility 47 can advantageously be integrated into the output apparatus 49, for example, in the case of an, in particular, resistive and/or capacitive input display.

The schematic representations contained in the drawings described do not reveal any scale or size relationships.

Finally, it should again be noted again that the methods described above in detail and the apparatuses disclosed are merely exemplary embodiments which can be modified by a person skilled in the art in a wide variety of ways without departing from the scope of the invention. Furthermore, the use of the indefinite article "a" or "an" does not preclude the possibility that the relevant features can also be present plurally. Similarly, the expressions "unit" and "element" do not preclude the components in question consisting of a plurality of cooperating subcomponents which can possibly also be spatially distributed.

The expression "based upon" can be understood in the context of the present application, in particular, in the sense of the expression "using". In particular, a formulation according to which a first feature is generated (alternatively: established, determined, etc.) based upon a second feature does not preclude the first feature being able to be generated (alternatively: established, determined, etc.) based upon a third feature.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a Graphics Processing Unit (GPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. An energy supply circuit for an X-ray device, the energy supply circuit comprising:

a voltage supply unit including a voltage supply input, an operating path and a maintenance path, the operating path configured to supply a plurality of components of the X-ray device for a normal operation, the maintenance path is configured to supply a subset of the plurality of components of the X-ray device for a maintenance operation; and a monitoring unit, the monitoring unit configured to detect an input voltage at the voltage supply input of the voltage supply unit via a sensor, wherein the voltage supply unit is configured to provide, dependent upon the detected input voltage, an electrical operating voltage via the operating path or an electrical maintenance voltage via the maintenance path to the subset of the plurality of components.

2. The energy supply circuit of claim 1, wherein the operating path is configured to supply at least one digital component and at least one analogue component of the X-ray device for a normal operation, and the maintenance path is configured to supply at least one of the at least one analogue component of the X-ray device for the maintenance operation.

3. The energy supply circuit of claim 2, wherein the maintenance path is a subpath of the operating path.

4. The energy supply circuit of claim 3, wherein the monitoring unit is configured to compare the detected input voltage with a specified voltage threshold value, if the detected input voltage is greater than or equal to the voltage threshold value, the voltage supply unit provides the electrical operating voltage via the operating path or, if the detected input voltage is less than the voltage threshold value, the voltage supply unit provides the electrical maintenance voltage via the maintenance path.

5. The energy supply circuit of claim 4, wherein the X-ray device has a detector unit and a conditioning unit, the conditioning unit is configured to provide an energy to maintain a maintenance state of the detector unit, and the maintenance path is configured to supply at least the conditioning unit.

6. The energy supply circuit of claim 5, wherein the detector unit has a semiconductor material and is configured to photon-count, and the conditioning unit is configured to keep the semiconductor material conditioned in the maintenance state via the energy provided.

7. The energy supply circuit of claim 5, wherein the conditioning unit is configured to provide the energy to maintain the maintenance state by at least one of heat transfer or illumination of the detector unit.

8. The energy supply circuit of claim 1, wherein the operating path and the maintenance path are different except the maintenance path is configured to supply the subset of the plurality of components of the X-ray device for the maintenance operation.

9. The energy supply circuit of claim 1, wherein the maintenance path is a subpath of the operating path.

10. The energy supply circuit of claim 1, wherein the monitoring unit is configured to compare the detected input voltage with a specified voltage threshold value, if the detected input voltage is greater than or equal to the voltage threshold value, the voltage supply unit provides the electrical operating voltage via the operating path or, if the detected input voltage is less than the voltage threshold value, the voltage supply unit provides the electrical maintenance voltage via the maintenance path.

11. The energy supply circuit of claim 1, wherein the X-ray device has a detector unit and a conditioning unit, the conditioning unit is configured to provide an energy to maintain a maintenance state of the detector unit, and the maintenance path is configured to supply at least the conditioning unit.

12. The energy supply circuit of claim 11, wherein the detector unit has a semiconductor material and is configured to photon-count, and the conditioning unit is configured to keep the semiconductor material conditioned in the maintenance state via the energy provided.

13. The energy supply circuit of claim 11, wherein the conditioning unit is configured to provide the energy to maintain the maintenance state by at least one of heat transfer or illumination of the detector unit.

14. An X-ray device comprising:

an X-ray source;

a detector unit;

at least one voltage source; and the energy supply circuit of claim 1, wherein the at least one voltage source optionally provides, in a first operating state, the electrical operating voltage or, in a second operating state, the electrical maintenance voltage as an input voltage to the energy supply circuit, wherein in the first operating state, based upon the input voltage to the energy supply circuit, the voltage supply unit provides the operating voltage via the operating path to the X-ray source and the detector unit for the normal operation such that X-ray radiation can be emitted via the X-ray source to irradiate the detector unit and the X-ray radiation can be detected via the detector unit, wherein in the second operating state, based upon the input voltage to the energy supply circuit, the voltage supply unit provides the maintenance voltage to the subset of the plurality of components of the X-ray device via the maintenance path for the maintenance operation.

15. The X-ray device of claim 14, comprising:

a first voltage source configured to provide the electrical operating voltage in the first operating state as the input voltage to the energy supply circuit; and a second voltage source, configured to provide the electrical maintenance voltage in the second operating state as the input voltage to the energy supply circuit.

16. The X-ray device of claim 14, further comprising:

a conditioning unit, wherein the conditioning unit is configured to provide an energy to maintain a maintenance state of the detector unit, the maintenance path is configured to supply at least the conditioning unit, and in the second operating state, based upon the input voltage to the energy supply circuit, the voltage supply unit provides the electrical maintenance voltage via the maintenance path to the conditioning unit.

17. The X-ray device of claim 14, wherein the X-ray device is a computed tomography system, and the X-ray source and the detector unit are rotatable in a defined arrangement.

18. A method for operating an X-ray device having the energy supply circuit of claim 1, comprising:

providing an input voltage to the energy supply circuit via at least one voltage source;

detecting the input voltage at the voltage supply input of the voltage supply unit via the sensor; and dependent upon the detected input voltage, providing the electrical operating voltage via the operating path or the electrical maintenance voltage via the maintenance path to the respective components of the X-ray device.

19. The method of claim 18, wherein the X-ray device has a detector unit and a conditioning unit, the conditioning unit is configured to provide an energy to maintain a maintenance state of the detector unit, the maintenance path is configured to supply at least the conditioning unit, dependent upon the detected input voltage, the voltage supply unit provides the operating voltage or the maintenance voltage to the conditioning unit, and in each case, via the conditioning unit, an energy to maintain the maintenance state of the detector unit is provided.

* * * * *